US012228567B2

(12) United States Patent
Yoon et al.

(10) Patent No.: US 12,228,567 B2
(45) Date of Patent: Feb. 18, 2025

(54) COLORIMETRIC SENSOR KIT FOR SCREENING THERAPEUTIC AGENT FOR NEURODEGENERATIVE DISEASE, INCLUDING AMYLOID SHELLED-GOLD NANOPARTICLE, AND METHOD FOR SCREENING THERAPEUTIC AGENT FOR NEURODEGENERATIVE DISEASE

(71) Applicant: Korea University Research and Business Foundation, Seoul (KR)

(72) Inventors: Dae Sung Yoon, Seoul (KR); Dong Tak Lee, Seoul (KR); In Su Kim, Seoul (KR); Gyu Do Lee, Namyangju-si (KR); Hyo Gi Jung, Daegu (KR); Yong Hwan Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 860 days.

(21) Appl. No.: 17/427,413

(22) PCT Filed: Nov. 1, 2019

(86) PCT No.: PCT/KR2019/014729
§ 371 (c)(1),
(2) Date: Jul. 30, 2021

(87) PCT Pub. No.: WO2020/166789
PCT Pub. Date: Aug. 20, 2020

(65) Prior Publication Data
US 2022/0099665 A1 Mar. 31, 2022

(30) Foreign Application Priority Data
Feb. 14, 2019 (KR) .................. 10-2019-0017328

(51) Int. Cl.
*G01N 33/543* (2006.01)
*A61P 25/28* (2006.01)
(Continued)

(52) U.S. Cl.
CPC ........ *G01N 33/54346* (2013.01); *A61P 25/28* (2018.01); *C12Q 1/6816* (2013.01);
(Continued)

(58) Field of Classification Search
CPC ......... G01N 33/54346; G01N 33/6896; G01N 2333/4709; G01N 2500/04; G01N 21/29;
(Continued)

(56) References Cited

FOREIGN PATENT DOCUMENTS

| KR | 10-1003124 B1 | 12/2010 |
| KR | 10-1082484 B1 | 11/2011 |

(Continued)

OTHER PUBLICATIONS

Sun, Yugang, and Younan Xia. "Gold and silver nanoparticles: a class of chromophores with colors tunable in the range from 400 to 750 nm." Analyst 128.6 (2003): 686-691. (Year: 2003).*

(Continued)

*Primary Examiner* — Jill A Warden
(74) *Attorney, Agent, or Firm* — Sughrue Mion, PLLC

(57) ABSTRACT

Disclosed are a colorimetric sensor kit for screening a therapeutic agent for a neurodegenerative disease, capable of easily detecting the degradation of amyloids by a drug, and a method for screening a therapeutic agent for a neurodegenerative disease.

4 Claims, 21 Drawing Sheets

(51) Int. Cl.
*C12Q 1/6816* (2018.01)
*G01N 33/68* (2006.01)
*B82Y 15/00* (2011.01)
*B82Y 30/00* (2011.01)

(52) U.S. Cl.
CPC .......... *G01N 33/6896* (2013.01); *B82Y 15/00* (2013.01); *B82Y 30/00* (2013.01)

(58) Field of Classification Search
CPC .. G01N 21/31; G01N 21/314; G01N 2500/20; A61P 25/28; C12Q 1/6816; B82Y 15/00; B82Y 30/00; C40B 30/04
See application file for complete search history.

(56) References Cited

FOREIGN PATENT DOCUMENTS

KR    10-2017-0133622 A       12/2017
KR       20170133622 A   *   12/2017

OTHER PUBLICATIONS

Han, Sun-Ho, et al. "Effective screen for amyloid B aggregation inhibitor using amyloid β-conjugated gold nanoparticles." International journal of nanomedicine (2011): 1-12. (Year: 2011).*

Geng, Jie, et al. "Rapid and efficient screening of Alzheimer's disease β-amyloid inhibitors using label-free gold nanoparticles." Molecular BioSystems 6.12 (2010): 2389-2391. (Year: 2010).*

Dongtak Lee et al., "Anti-Aβ drug candidates in clinical trials and plasmonic nanoparticle-based drug-screen for Alzheimer's disease", Analyst, Mar. 2018, pp. 2204-2212, vol. 143.

Sun-Ho Han et al., "Effective screen for amyloid β aggregation inhibitor using amyloid β-conjugated gold nanoparticles", International Journal of Nanomedicine, 2011, pp. 1-12, vol. 6.

Hy Kim et al., "A gold nanoparticle-mediated rapid in vitro assay of anti-aggregation reagents for amyloid β and its validation", Chemical Communications, 2017, pp. 4449-4452, vol. 53, No. 32.

Daniel Aili et al., "Bioresponsive peptide-inorganic hybrid nanomaterials", Chemical Society Reviews, 2010, pp. 3358-3370, vol. 39, No. 9.

Ganchao Chen et al., "A general colorimetric method for detecting protease activity based on peptide-induced gold nanoparticle aggregation", RSC Advances, Communication, 2014, pp. 6560-6563, vol. 4.

International Search Report for PCT/KR2019/014729 dated Feb. 7, 2020 [PCT/ISA/210].

Written Opinion for PCT/KR2019/014729 dated Feb. 7, 2020 [PCT/ISA/237].

* cited by examiner

G

| Category | EPPS | Curcumin | Glutathion | Rutin hydrate | Eptifibatide acetate | Tramiprosate |
|---|---|---|---|---|---|---|
| | 0.99 | 0.99 | N.A. | 0.87 | 0.98 | N.A. |
| | 0.9722 | 7.421 | N.A. | 13.9 | 4.462 | N.A. |
| | 7.691 | 3.994 | N.A. | 5.034 | 5.85 | N.A. |
| | 0.7938 | 0.155 | N.A. | 0.060 | 0.168 | N.A. |

COLORIMETRIC SENSOR KIT FOR SCREENING THERAPEUTIC AGENT FOR NEURODEGENERATIVE DISEASE, INCLUDING AMYLOID SHELLED-GOLD NANOPARTICLE, AND METHOD FOR SCREENING THERAPEUTIC AGENT FOR NEURODEGENERATIVE DISEASE

CROSS REFERENCE TO RELATED APPLICATION

This application is a National Stage of International Application No. PCT/KR2019/014729 filed Nov. 1, 2019, claiming priority based on Korean Patent Application No. 10-2019-0017328 filed Feb. 14, 2019.

TECHNICAL FIELD

The present disclosure relates to a colorimetric sensor kit for screening a therapeutic agent for a neurodegenerative disease, including an amyloid shelled-gold nanoparticle, and a method for screening therapeutic agent for a neurodegenerative disease.

BACKGROUND ART

Degenerative brain disease refers to a disease occurring in the brain with aging. It is known that specific brain cell groups in the brain slowly lose their function, the brain nerve cells most important for signal transduction of the central nervous system are killed, the shape or function of synapses that exchange information between brain nerve cells is degraded, and the electrical activity of the cranial nerve is increased or decreased abnormally due to currently unknown reasons.

The most representative symptom or prognosis of Alzheimer's disease known thus far is the accumulation and aggregation of beta-amyloid (Aβ). As a result, beta-amyloid plaques occur in the brain of a patient.

Among the beta-amyloids, beta-amyloid 42 ($A\beta_{42}$) has very high pathotoxicity. It forms fibrils by aggregating in large quantities and the fibrils form plaques. Therefore, it is the major cause of Alzheimer's disease since it induces amyloid aggregation.

Therapeutic agents targeting the beta-amyloid 42, which has been known as one of the major causes of Alzheimer's disease, are being developed actively. For example, after synthesizing beta-amyloid fibrils and beta-amyloid plaques and adding a drug candidate to the synthesized substances, the degradation of the drug is investigated by atomic force microscopy, transmission electron microscopy, etc. or the degradation of $A\beta_{42}$ is monitored by adding a fluorescent substance.

However, there are problems that $A\beta_{42}$ is very expensive and a long time is required for the synthesis of the beta-amyloid fibrils and beta-amyloid plaques.

Since a therapeutic agent for Alzheimer's disease has not been found yet and the only available therapy is to slow the progression of the disease, a technology for treating a neurodegenerative disease such as Alzheimer's disease is necessary.

DISCLOSURE

Technical Problem

The present disclosure is directed to providing a colorimetric sensor kit for screening a therapeutic agent for a neurodegenerative disease, capable of easily detecting the degradation of amyloids by a drug, and a method for screening a therapeutic agent for a neurodegenerative disease.

Technical Solution

In an exemplary embodiment, the present disclosure provides a colorimetric sensor kit for screening a therapeutic agent for a neurodegenerative disease, which includes an amyloid shelled-gold nanoparticle wherein an amyloid aggregate is formed as an amyloid oligomer is coated on the surface of a gold nanoparticle.

In another exemplary embodiment, the present disclosure provides a method for screening a therapeutic agent for a neurodegenerative disease, which includes:
i) a step of preparing an amyloid shelled-gold nanoparticle wherein an amyloid aggregate is formed as an amyloid oligomer is coated on the surface of a gold nanoparticle;
ii) a step of treating the amyloid shelled-gold nanoparticle with a drug candidate for a therapeutic agent for a neurodegenerative disease; and
iii) a step of comparing color change of the amyloid shelled-gold nanoparticle before and after the treatment with the drug candidate.

Advantageous Effects

A colorimetric sensor kit for screening a therapeutic agent for a neurodegenerative disease and a method for screening a therapeutic agent for a neurodegenerative disease according to the present disclosure allow easy screening of a therapeutic agent for a neurodegenerative disease using an amyloid shelled-gold nanoparticle wherein an amyloid aggregate is formed.

In particular, high-throughput drug screening is possible by treating the composite with a group of drug candidates targeting amyloid proteins and comparing the color change of the amyloid shelled-gold nanoparticle before and after the treatment with the drug candidates and, therefore, the time and cost required for selecting a new drug candidate can be saved.

Figure 4:
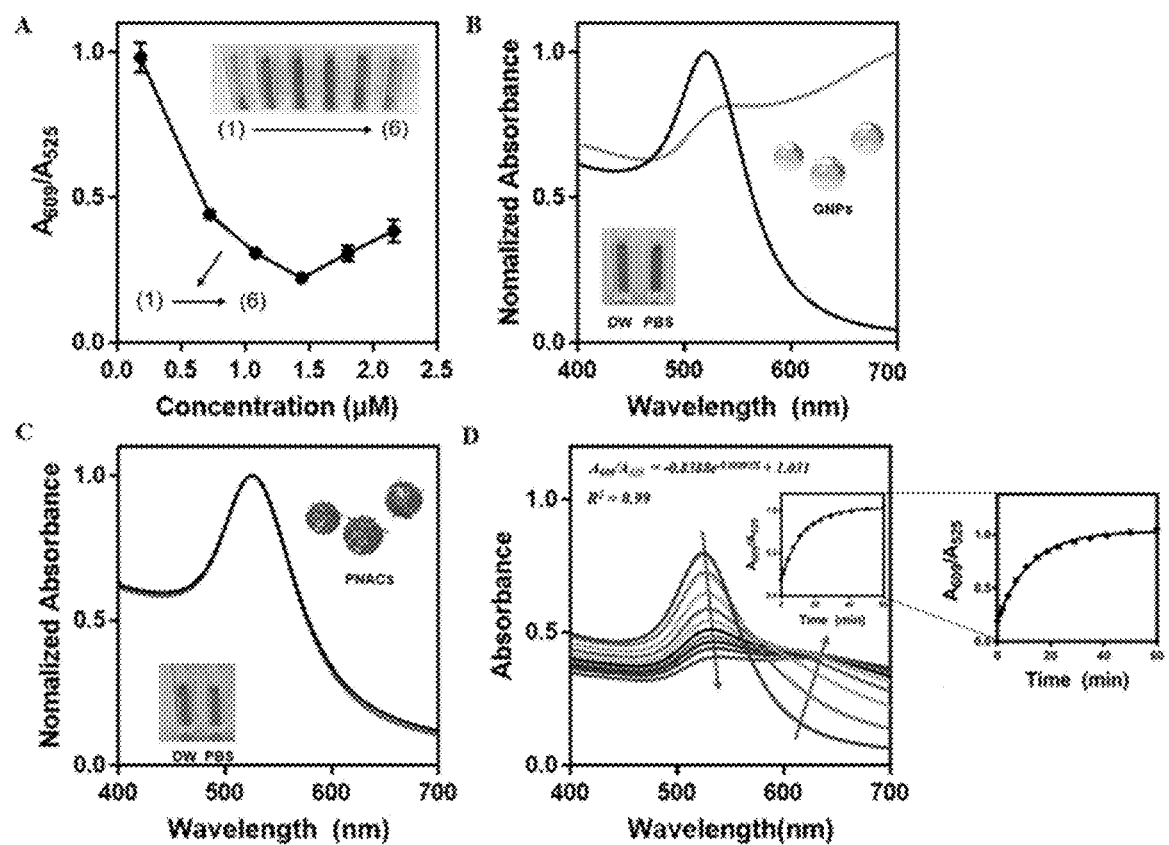

A of FIG. 4 shows the images and the shift of relative absorbance ($A_{609}/A_{525}$) of ASGN solutions of an example depending on the Aβ monomer concentration, B of FIG. 4 shows the shift of $A_{609}/A_{525}$ of a gold nanoparticle solution of a comparative example using a buffer solution, C of FIG. 4 shows the shift of $A_{609}/A_{525}$ of ASGN solutions of the example depending on the type of buffer solutions, and D of FIG. 4 the shift of relative absorbance ($A_{609}/A_{525}$) of ASGN solutions of the example in a protease XIV solution depending on time.

FIGS. 5A to 5K show a result of kinetic analysis of an Aβ-degrading enzyme using ASGN of an example.

Figure 6:
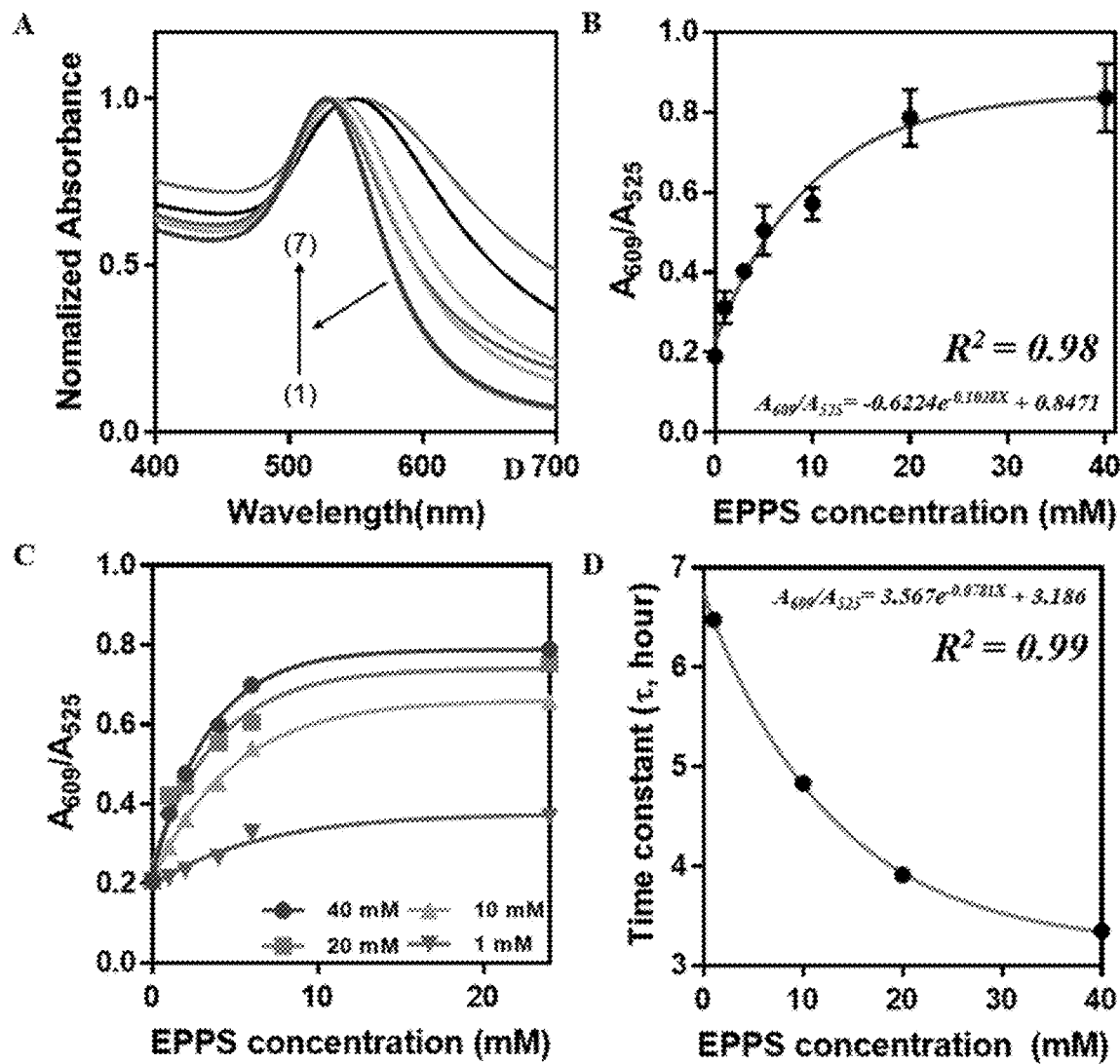

FIG. 6 shows a result of kinetic analysis of an Aβ-degrading agent (EPPS).

Figure 7A:
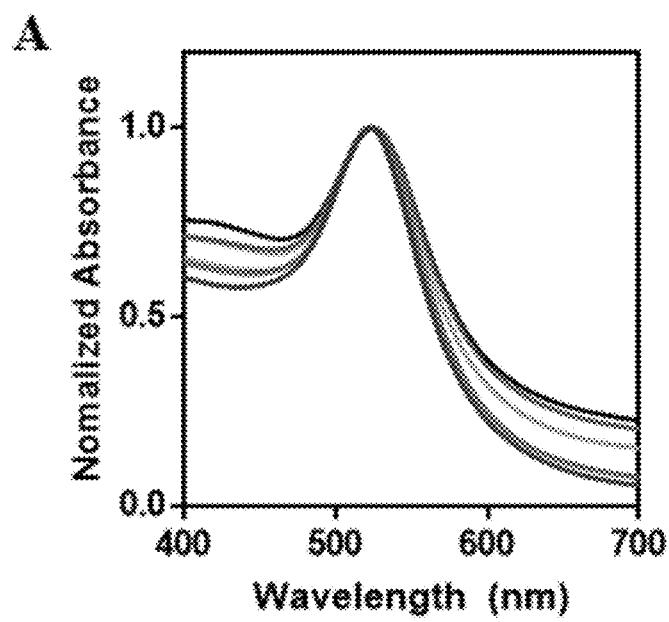
Figure 7B:
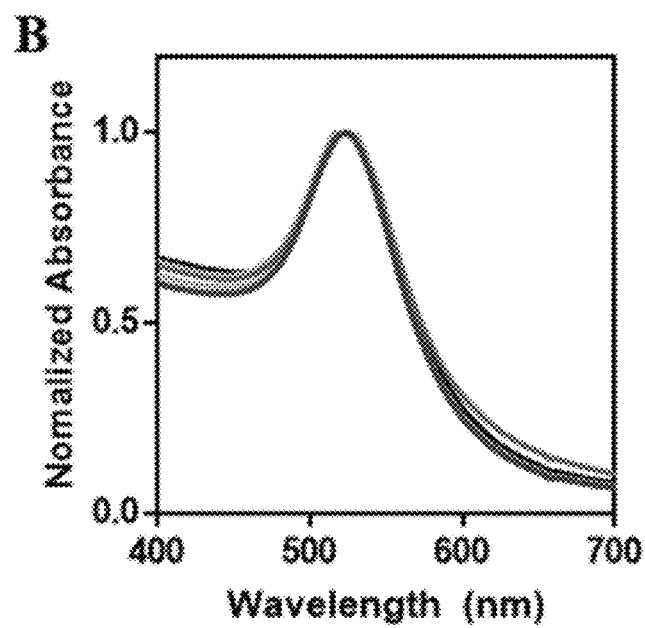
Figure 7C:
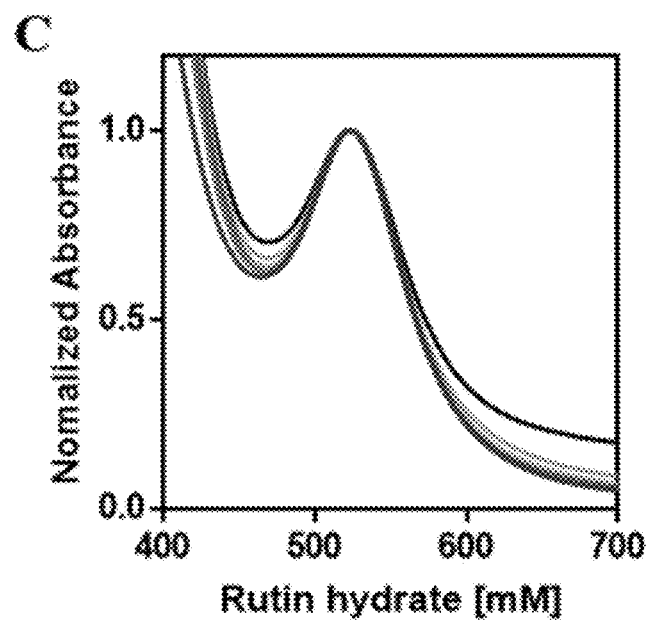
Figure 7D:
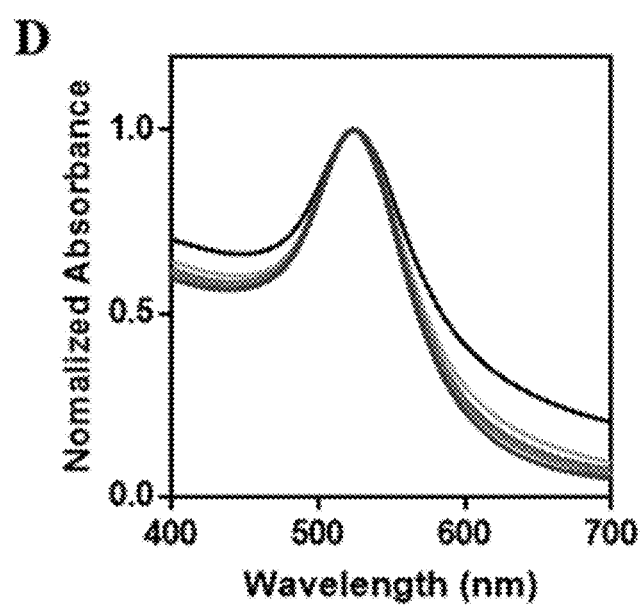
Figure 7E:
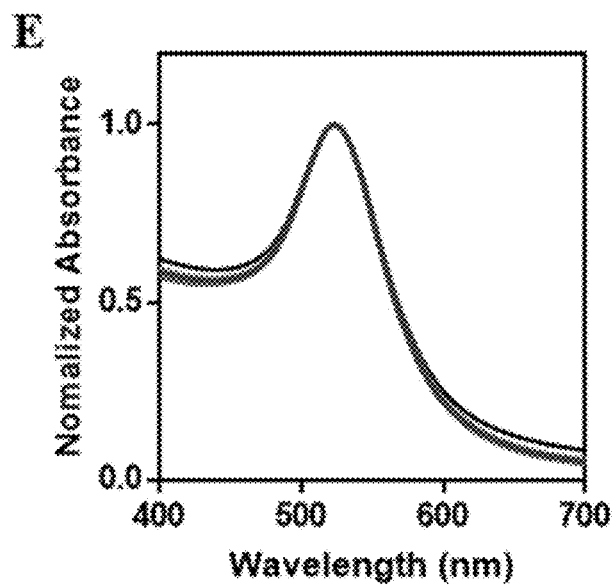
Figure 7F:
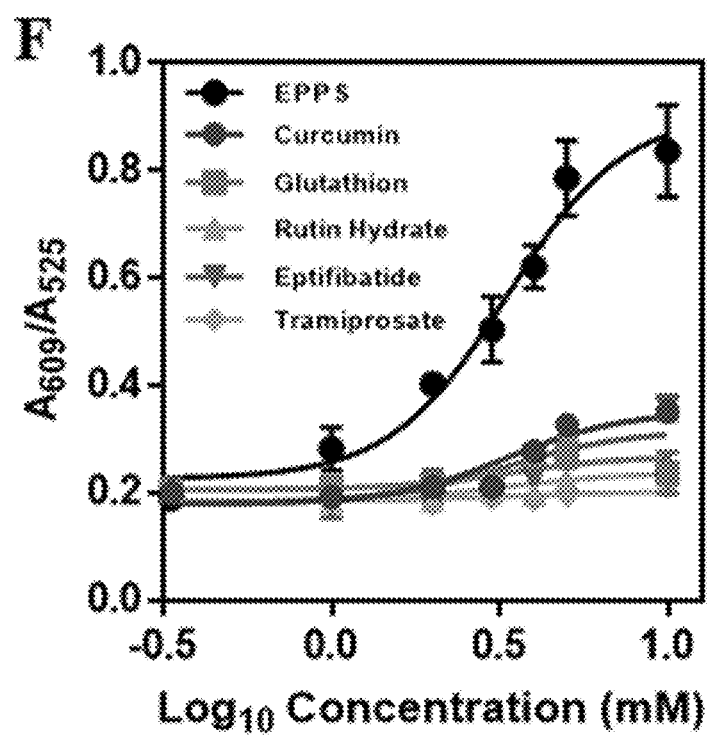
Figures 7G, 7H:
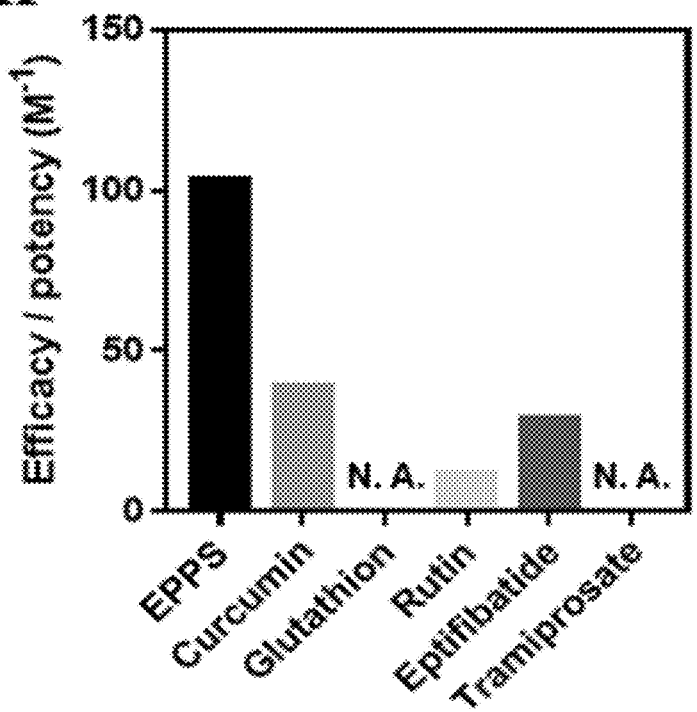

FIGS. 7A to 7E show a result of investigating the effect of curcumin, glutathione, rutin hydrate, eptifibatide acetate and tramiprosate, which are drugs helpful for treatment of Alzheimer's disease, FIG. 7F shows dose-dependent curves for the result of FIGS. 7A to 7E, and FIGS. 7G and 7H show a result of evaluating the efficacy/potency ($M^{-1}$) of the drugs.

BEST MODE

The present disclosure may be changed variously and may have various exemplary embodiments. Hereinafter, specific exemplary embodiments will be described in detail referring to drawings.

However, it should be understood that the present disclosure is not limited to the specific exemplary embodiments but includes all changes, equivalents and substitutes included in the technical idea and scope of the present disclosure. When describing the present disclosure, a detailed description of known functions and configurations will be omitted when it may make the subject matter of the present disclosure unclear.

The terms used in the present disclosure are used merely to describe specific exemplary embodiments and are not intended to limit the present disclosure. As used herein, a singular expression includes a plural expression unless the context expressly indicates otherwise.

In the present disclosure, the terms "comprise (contain or include)", "have", etc. are used to specify the presence of stated features, numbers, steps, actions, elements, components or combinations thereof, but do not preclude the presence or addition of one or more other features, numbers, steps, actions, elements, components or combinations thereof.

The present disclosure relates to a colorimetric sensor kit for screening a therapeutic agent for a neurodegenerative disease, including an amyloid shelled-gold nanoparticle, and a method for screening therapeutic agent for a neurodegenerative disease.

In the present disclosure, an "amyloid shelled-gold nanoparticle" refers to a composite in which an amyloid oligomer is coated on the surface of a gold nanoparticle. More specifically, it may refer to a composite in which an amyloid aggregate is formed as an amyloid oligomer is coated on the surface of a gold nanoparticle The term 'amyloid protein' used in the present disclosure refers to a protein capable of forming an amyloid or a fragment thereof. The terms 'amyloid deposit', 'amyloid aggregate', 'amyloid fibril', etc. refer to a protein deposit which causes a disease, formed from misfolding of the protein that changes the random coil or α-helical structure of a secondary or tertiary structure into a β-sheet, and an 'amyloid protein monomer' refers to the protein before the conformational change occurs.

The amyloid oligomer, which is coated on the surface of the gold nanoparticle, may provide steric stabilization such that the gold nanoparticle is not aggregated in solution. In particular, when the composite is treated with a group of drug candidates targeting the amyloid protein, if the drug candidate has an effect of degrading the aggregate of the amyloid protein, the surface of the gold nanoparticle is exposed as the amyloid aggregate is degraded and, accordingly, the gold nanoparticle is aggregated. The aggregation of the gold nanoparticle causes the change in optical properties. Therefore, the amyloid shelled-gold nanoparticle exhibits color change as compared to the composite not treated with the drug candidate. For example, the color change of the composite may occur due to localized surface plasmon resonance (LSPR) by the aggregated gold nanoparticle.

In the present disclosure, any nanomaterial that exhibits LSPR may be used as the nanoparticle. Specifically, a gold nanoparticle, a gold nanorod, etc. may be used Although a gold nanoparticle is used as the nanoparticle in an example of the present disclosure, an organic nanoparticle or a non-organic nanoparticle such as an inorganic or metal nanoparticle may also be used.

By detecting the color change, the present disclosure allows the investigation of the degradation effect of the amyloid aggregate and thus enables high-throughput drug screening, etc. That is to say, high-throughput drug screening can be conducted using a colorimetric sensor kit for screening a therapeutic agent for a neurodegenerative disease according to the present disclosure by detecting the color change of the composite before and after the treatment with the drug candidate.

The color change may be measured with naked eyes or using a spectrometer, a colorimeter, etc. Any instrument capable of measuring color change may be used.

The drug candidate refers to a drug candidate for a therapeutic agent for a neurodegenerative disease. In a specific exemplary embodiment, it is an agent which degrades the amyloid aggregate. Specifically, an amyloid-targeting drug for treating Alzheimer's disease may be an amyloid formation inhibitor, an amyloid aggregation inhibitor, an aggregate-degrading agent, etc. The present disclosure allows the screening of drugs and enzymes that can degrade the amyloid aggregate.

In the present disclosure, the "neurodegenerative disease" refers to a disease deeply related with aging, wherein abnormal nerve cell death occurs rapidly in a part of the nervous system or the entire brain unlike the normal process of aging, leading to decline in the function of the brain and the spinal cord, cognitive ability, gait and motor ability, etc. More specifically, the neurodegenerative disease may be selected from a group consisting of Alzheimer's disease, Parkinson's disease, Lou Gehrig's disease, Huntington's disease, multiple sclerosis, stroke or dementia. For example, the neurodegenerative disease of the present disclosure may refer to Alzheimer's disease.

The "amyloid protein" refers to an aggregate of proteins formed from the aggregation of β-sheet structures. The β-sheet aggregation of the amyloid protein may be associated with a number of diseases.

More specifically, the amyloid protein may refer to a protein that can form an amyloid deposit selected from a group consisting of β-amyloid and tau protein of Alzheimer's disease, α-synuclein of Parkinson's disease, huntingtin of Huntington's disease, prion of prion diseases, amylin of type 2 diabetes, immunoglobulin of systemic amyloidosis, serum amyloid A and transthyretin, or a fragment thereof. For example, the amyloid protein may refer to β-amyloid of Alzheimer's disease, and may be used interchangeably with β-amyloid 42, $A\beta_{42}$ or Aβ.

Hereinafter, the present disclosure is described in detail.

In an exemplary embodiment, the present disclosure provides a colorimetric sensor kit for screening a therapeutic agent for a neurodegenerative disease, which includes an amyloid shelled-gold nanoparticle wherein an amyloid aggregate is formed as an amyloid oligomer is coated on the surface of a gold nanoparticle.

In particular, the kit may further include a tool for measuring color change occurring as the amyloid of the amyloid shelled-gold nanoparticle is degraded by a drug. The tool for measuring color change may be any tool for measuring color change, such as a spectrometer or a colorimeter. In a specific exemplary embodiment, the color change may be measured with naked eyes.

For example, the color change of the amyloid shelled-gold nanoparticle may be compared before and after treating with a drug candidate. More specifically, the amyloid shelled-gold nanoparticle not treated with a drug candidate may exhibit red color, and it may exhibit red color when treated with a drug candidate as the amyloid aggregate is degraded. In this case, the drug candidate may be screened as a therapeutic agent for a neurodegenerative disease.

Figure 1A:
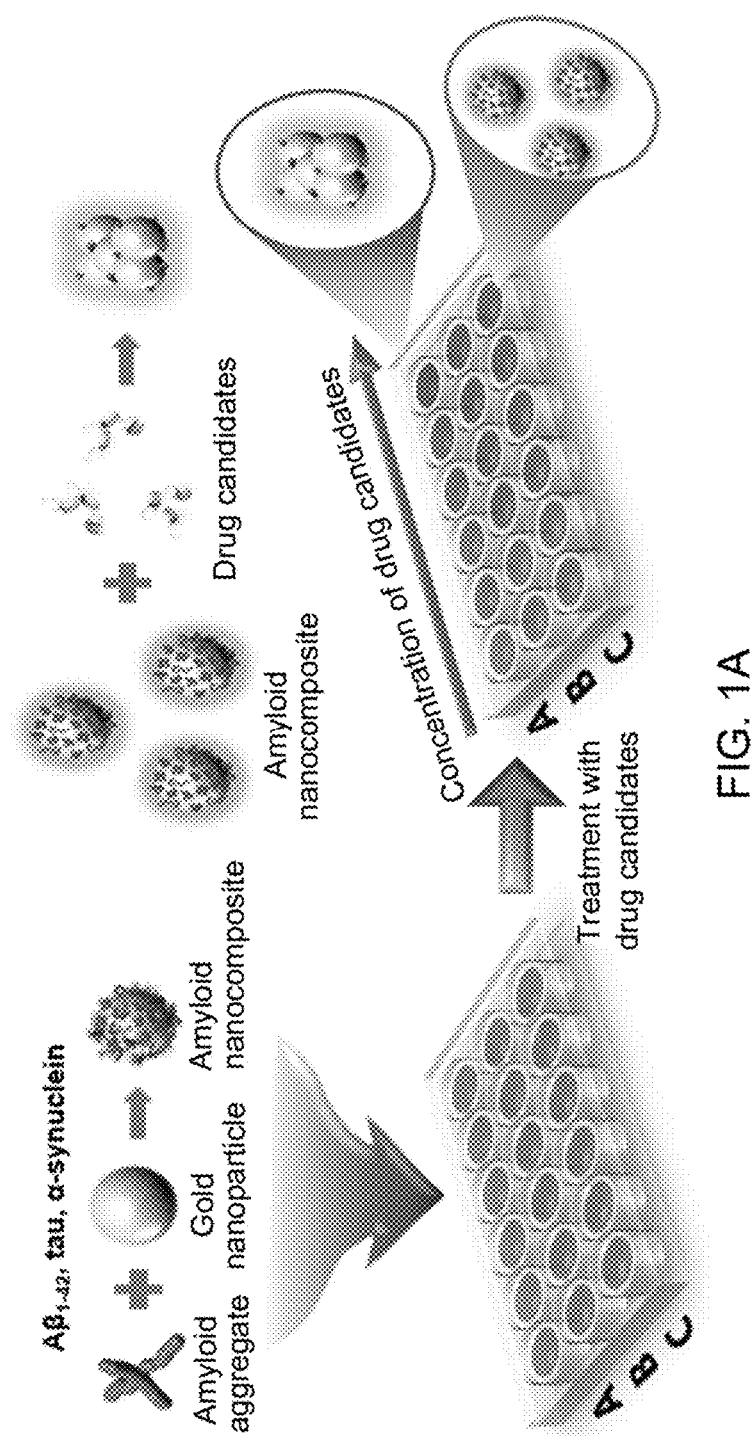
FIGS. 1A and 1B show the principle of drug screening of a colorimetric sensor kit for screening a therapeutic agent for a neurodegenerative disease according to the present disclosure (FIG. 1A: treatment with drug candidate, FIG. 1B: color change of solution depending on reaction with drug).
Figure 1B:
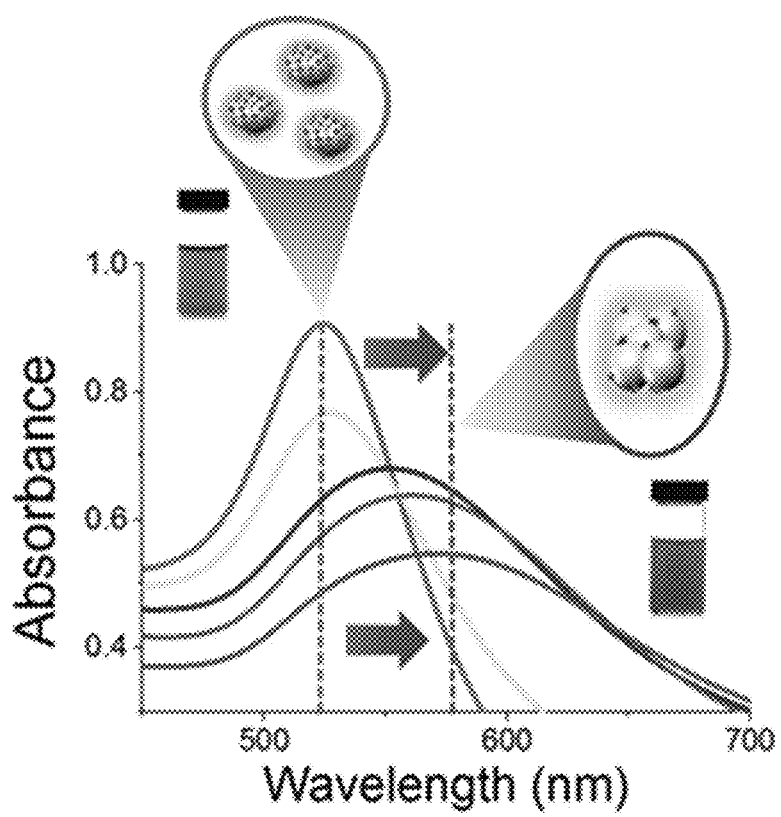

FIGS. 1A and 1B show the principle of drug screening of a colorimetric sensor kit for screening a therapeutic agent for a neurodegenerative disease according to the present disclosure (FIG. 1A: treatment with drug candidate, FIG. 1B: color change of solution depending on reaction with drug). The operating principle of the colorimetric sensor kit for screening a therapeutic agent for a neurodegenerative disease of the present disclosure will be described in detail referring to FIGS. 1A and 1B.

Since the amyloid protein covers the surface of a gold nanoparticle, the composite is sterically stabilized and thus can be easily dispersed in solution (PBS buffer or Tris buffer). In particular, as a result of the action of an enzyme or a drug which degrades the amyloid protein, the amyloid protein covering the surface of the gold nanoparticle is degraded as time goes by and is separated from the surface of the gold nanoparticle. The gold nanoparticle separated from the amyloid protein is aggregated under a high salt concentration, leading to color change in the solution.

In contrast, for a drug which is not effective for the amyloid protein, the amyloid protein is not degraded in solution and the gold nanoparticle is not aggregated. Therefore, the color change of the solution does not occur.

For example, if the color of the solution is changed from red to blue as the amyloid aggregate is degraded by treating with the drug candidate, the drug candidate may be screened as a therapeutic agent for a neurodegenerative disease. The color change may be determined with naked eyes or using a spectrometer or a colorimeter.

As described above, the amyloid shelled-gold nanoparticle may refer to a composite wherein the amyloid aggregate is formed on the surface of a gold nanoparticle as the amyloid oligomer is coated on the surface of the gold nanoparticle. That is to say, the gold nanoparticle may form a core of the composite, and the amyloid protein may form a shell on the surface of the core metal.

In particular, the amyloid shelled-gold nanoparticle allows the coating of the amyloid protein on the surface of the gold nanoparticle due to coulombic interaction between the negative charge of the gold particle surface and the positive charge of the N-terminal of the amyloid protein and, additionally, the formation of an amyloid with a β-sheet structure. For this reason, the amyloid-gold nanoparticle composite can be formed even without a specific ligand.

For example, a positively charged gold nanoparticle may be capped with a positively charged material, and a negatively charged gold nanoparticle may be capped with a negatively charged material. The negatively charged material may be citrate, although not being necessarily limited thereto.

The amyloid oligomer may provide steric stabilization such that the gold nanoparticle is not aggregated in solution as it is coated on the surface of the gold nanoparticle. In particular, when the composite is treated with a group of drug candidates targeting the amyloid protein, if a drug candidate exhibits an effect of degrading the aggregate of the amyloid protein, the surface of the gold nanoparticle is exposed as the amyloid aggregate is degraded and, accordingly, the gold nanoparticle is aggregated. In addition, the aggregation of the gold nanoparticle results in the change in optical properties, which leads to color change of the amyloid shelled-gold nanoparticle as compared to the composite not treated with the drug candidate.

In the present disclosure, the amyloid aggregate degradation effect may be detected by detecting the color change. This allows high-throughput drug screening, etc. That is to say, the colorimetric sensor kit for screening a therapeutic agent for a neurodegenerative disease according to the present disclosure allows high-throughput drug screening by detecting the color change of the composite before and after the treatment with the drug candidate.

Here, the amyloid protein refers to an aggregate of proteins formed from the aggregation of β-sheet structures. The β-sheet aggregation of the amyloid protein may be associated with a number of diseases.

More specifically, the amyloid protein may refer to a protein that can form an amyloid deposit selected from a group consisting of β-amyloid and tau protein of Alzheimer's disease, α-synuclein of Parkinson's disease, huntingtin of Huntington's disease, prion of prion diseases, amylin of type 2 diabetes, immunoglobulin of systemic amyloidosis, serum amyloid A and transthyretin, or a fragment thereof. For example, the amyloid protein may refer to β-amyloid of Alzheimer's disease.

In the present disclosure, "nano" includes the range of size understood by those of ordinary skill in the art. Specifically, the size range may be from 0.1 to 1000 nm, more specifically from 10 to 1000 nm, further more specifically from 10 to 500 nm, even more specifically from 10 to 250 nm.

In addition, the gold nanoparticle may have an average diameter of 10-50 nm. In a specific exemplary embodiment, if the average diameter of the gold nanoparticle is smaller than 10 nm, the amyloid protein may not be attached because the curvature of the gold nanoparticle is large. And, if the average diameter of the gold nanoparticle exceeds 50 nm, the localized surface plasmon resonance of the old nanoparticle itself is decreased significantly. Accordingly, it is preferred that the gold nanoparticle has an average diameter of 10-50 nm.

In addition, the amyloid oligomer which forms the shell of the gold nanoparticle may have an average thickness of 1-3 nm. In a specific exemplary embodiment, if the average thickness of the amyloid oligomer is smaller than 1 nm, the protein may be seen as a monomer rather than an oligomer. And, the average thickness of the amyloid oligomer exceeds 3 nm, it may be seen as an amyloid fiber. Accordingly, it is preferred that the amyloid oligomer which forms the shell of the gold nanoparticle has an average thickness of 1-3 nm, specifically 2-3 nm.

For example, the amyloid shelled-gold nanoparticle may have an average diameter of 15-50 nm.

The amyloid shelled-gold nanoparticle may be obtained by mixing the amyloid protein and the gold nanoparticle at a ratio of 100-2250:1. If the ratio of the amyloid protein to the gold nanoparticle exceeds 1400, a fibril is formed rather than an oligomer. And, if the volume ratio of the amyloid protein to the gold nanoparticle is smaller than 1400, the gold nanoparticle may not be covered enough. Therefore, the above-described range is preferred. For example, an optimum ratio of the β-amyloid and the gold nanoparticle is 1400:1 for an amyloid with a thickness of 2-3 nm.

In another exemplary embodiment, the present disclosure provides a method for screening a therapeutic agent for a neurodegenerative disease, which includes:
 i) a step of preparing an amyloid shelled-gold nanoparticle wherein an amyloid aggregate is formed as an amyloid oligomer is coated on the surface of a gold nanoparticle;
 ii) a step of treating the amyloid shelled-gold nanoparticle with a drug candidate for a therapeutic agent for a neurodegenerative disease; and
 iii) a step of comparing color change of the amyloid shelled-gold nanoparticle before and after the treatment with the drug candidate.

Here, as described above, the amyloid protein may refer to a protein that can form an amyloid deposit selected from a group consisting of β-amyloid and tau protein of Alzheimer's disease, α-synuclein of Parkinson's disease, huntingtin of Huntington's disease, prion of prion diseases, amylin of type 2 diabetes, immunoglobulin of systemic amyloidosis, serum amyloid A and transthyretin, or a fragment thereof. For example, the amyloid protein may refer to β-amyloid of Alzheimer's disease.

In particular, the color change may be measured with naked eyes or using a spectrometer or a colorimeter.

Furthermore, after the step iii), a step iv) of screening the drug candidate as a therapeutic agent for a neurodegenerative disease if the amyloid shelled-gold nanoparticle exhibits red color before treating with the drug candidate and its color changes from red to blue when treated with the drug candidate as the amyloid protein aggregate is degraded may be further included.

More specifically, the amyloid shelled-gold nanoparticle exhibiting red color may have a maximum absorbance at 525 nm, and have a maximum absorbance at 609 nm when its color changes from red to blue by treatment with the drug candidate as the amyloid protein aggregate is degraded.

In the present disclosure, a therapeutic agent for a neurodegenerative disease is screened based on the color change of the drug candidate included in the amyloid shelled-gold nanoparticle. For a control group wherein a drug candidate is not included in the kit and a test group wherein a drug candidate is included, the color change of the composite is compared after a predetermined time.

If the color changes from red to blue by the treatment with the drug candidate as the amyloid aggregate is degraded, it can be seen that the drug candidate may be utilized as a therapeutic agent for a neurodegenerative disease.

MODE FOR INVENTION

Hereinafter, the present disclosure is described in more detail through examples and test examples.

However, the following examples and test examples are only for illustrating the present disclosure and the contents of the present disclosure are not limited by the examples and test examples.

Preparation Example

Synthesis of Gold Nanoparticle

A gold nanoparticle was prepared by 'hydrothermal synthesis' whereby a precursor chloroauric acid ($HAuCl_4$) was reduced by applying heat using sodium citrate as a surface stabilizer. The size of the nanoparticle was controlled with the amount of the surface stabilizer.

Specifically, after preparing stock solutions by dissolving 2.55 mL of $HAuCl_4$ in 47.5 mL of distilled water and 108.8 mg of sodium citrate in 10 mL of distilled water, the $HAuCl_4$ solution was heated under stirring and 0.9 mL of the sodium citrate solution was added when the solution began to boil. The mixture solution was boiled for 15 minutes and then stored.

Then, a gold nanoparticle with a diameter of about 20 nm was synthesized by washing the gold nanoparticle stabilized with citric acid at 10,000 rpm for 5 minutes.

Purification of β-Amyloid (Aβ)

1 mg of freeze-dried Aβ peptide was dissolved in 230 μL of 1,1,1,3,3,3-hexafluoro-2-propanol (HFIP) and then kept at room temperature for 1 hour. Then, after transferring an adequate amount of the solution (Aβ solution) to a microcentrifuge tube, the solution was freeze-dried in SpeedVac in vacuo for 2 hours and the tube was kept at −20° C. for further experiment.

Thereafter, the freeze-dried solution was transferred to a vacuum concentrator (SpeedVac) and the remaining HFIP and water were removed by centrifuging at −20° C. in vacuo at 1500 rpm for 1 hour. The purified substance was stored at −20° C. as a stock solution until use.

EXAMPLES

Purification of Amyloid Shelled-Gold Nanoparticle

An amyloid shelled-gold nanoparticle was prepared by coating the purified Aβ on the surface of the gold nanoparticle synthesized in Preparation Example.

Specifically, a solution containing the gold nanoparticle synthesized in Preparation Example was centrifuged at 10,000 rpm for 30 minutes and 0.07 μL was obtained by removing the supernatant. Subsequently, the purified Aβ was diluted with DW to 10 μM and incubated at 37° C. for 3 hours.

Thereafter, the diluted Aβ and the gold nanoparticle solution were mixed at a ratio of 160 μL:70 μL and then stirred. Then, an Aβ-gold nanoparticle composite was prepared by incubating the solution containing the Aβ and the gold nanoparticle (hereinafter, referred to as an Aβ-gold nanoparticle solution) at 37° C. for 24 hours in a thermomixer rotating at 120 rpm. Then, DW was added such that the total volume of the prepared solution was 1 mL.

Then, an amyloid-gold nanoparticle composite (Aβ-shelled gold nanoparticle, ASGN) was synthesized as shown in FIGS. 2A to 2E.

Figure 2A:
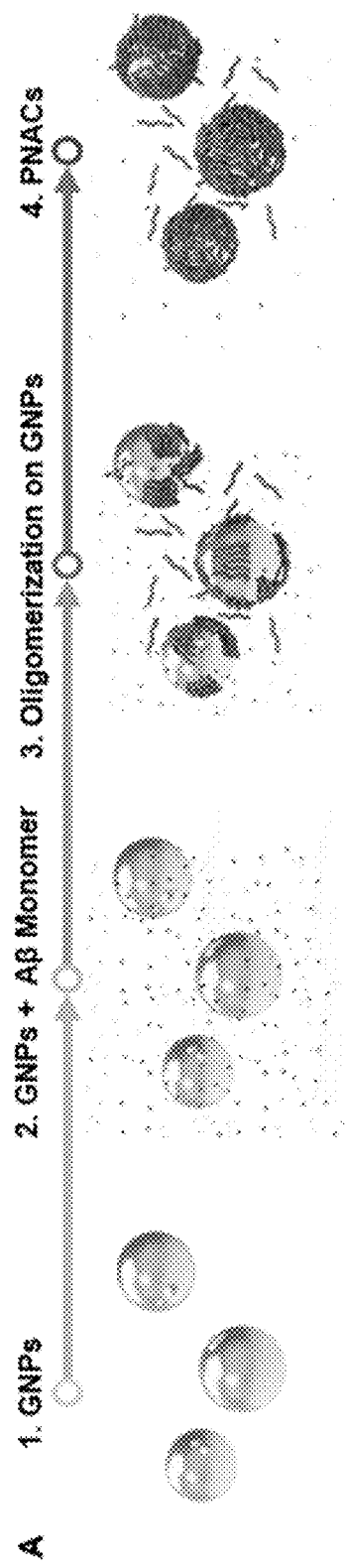
FIG. 2A describes a method of synthesizing an amyloid shelled-gold nanoparticle (ASGN) using catalyst characteristics.
Figure 2B:
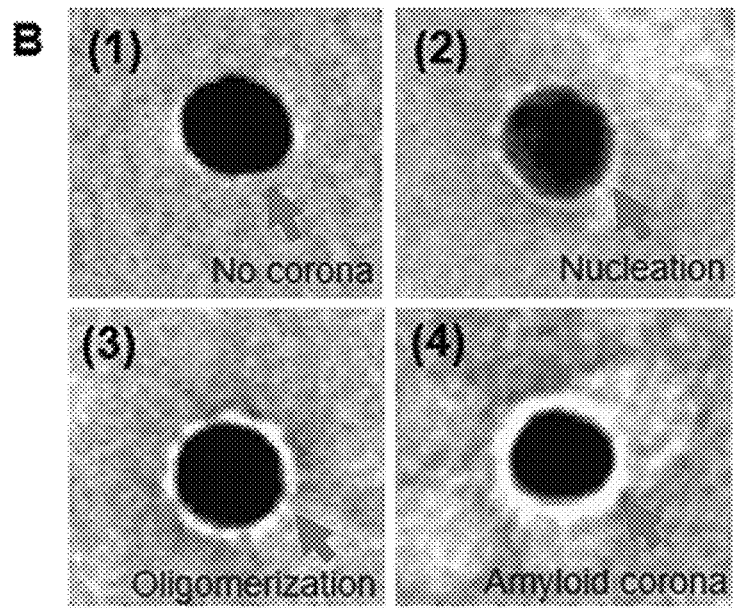
FIG. 2B shows HRTEM images obtained during the synthesis of ASGN ((1): gold nanoparticle, (2, 3): intermediate of ASGN synthesis, (4): ASGN)
Figure 2C:
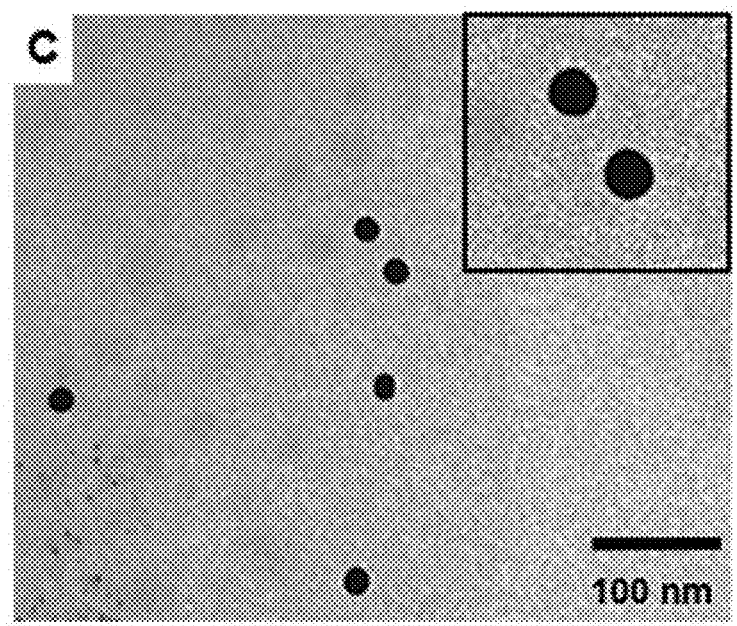
FIG. 2C shows an HRTEM image of gold nanoparticles.
Figure 2D:
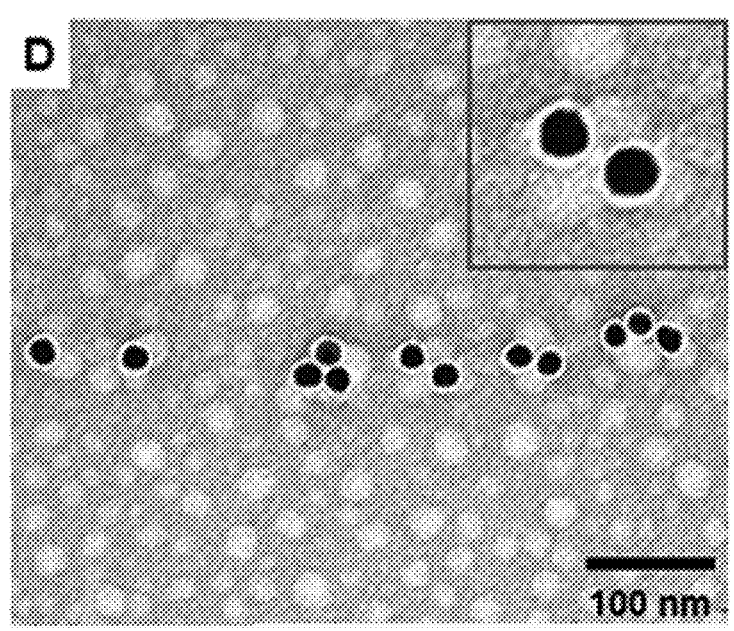
FIG. 2D shows an HRTEM image of ASGNs.
Figure 2E:
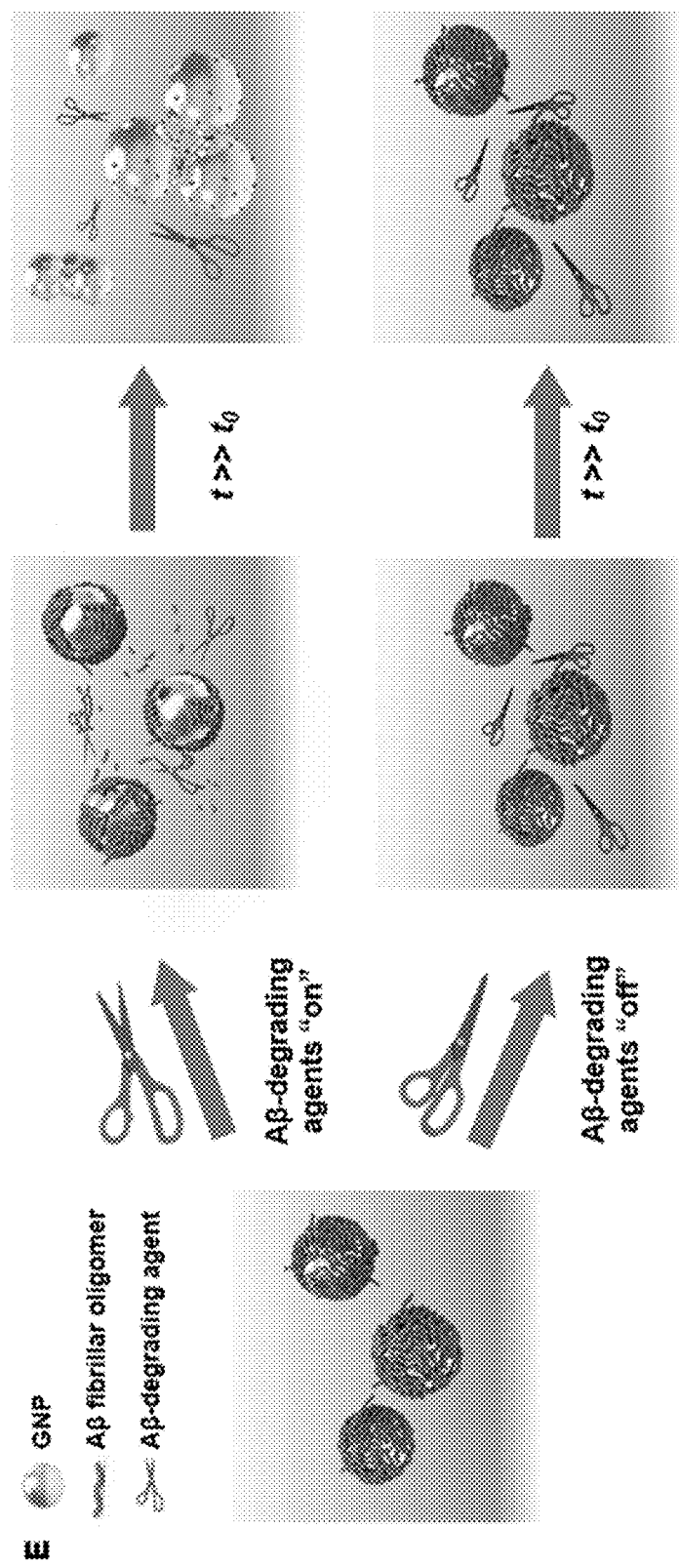
FIG. 2E schematically describes an anti-Aβ drug screening process using ASGN.

FIG. 2A describes a method of synthesizing an amyloid shelled-gold nanoparticle (ASGN) using catalyst characteristics, FIG. 2B shows HRTEM images obtained during the synthesis of ASGN ((1): gold nanoparticle, (2, 3): intermediate of ASGN synthesis, (4): ASGN), FIG. 2C shows an HRTEM image of gold nanoparticles, and FIG. 2D shows an HRTEM image of ASGNs. FIG. 2E schematically describes an anti-Aβ drug screening process using ASGN.

Referring to FIGS. 2A to 2E, an amyloid-gold nanoparticle composite is formed as the Aβ monomer is attached on the surface of a gold nanoparticle and oligomerization occurs. The process and result can be identified from FIGS. 2B-2D. The synthesized amyloid-gold nanoparticle composite can realize a drug screening mechanism whereby the color of the solution is changed as the amyloid on the surface is degraded, as shown in FIG. 2E.

Comparative Example

A gold nanoparticle was prepared in the same manner as in Example except that the amyloid protein was coated on the surface of the gold nanoparticle.

Test Example

Test Example 1. Characterization of Amyloid-Gold Nanoparticle Composite

For investigation of the amyloid on the surface of the amyloid-gold nanoparticle composite prepared in Example, graphene sensors having different antibodies were prepared and reacted with the composite. The result is shown in FIGS. 3A to 3E.

Figure 3A:
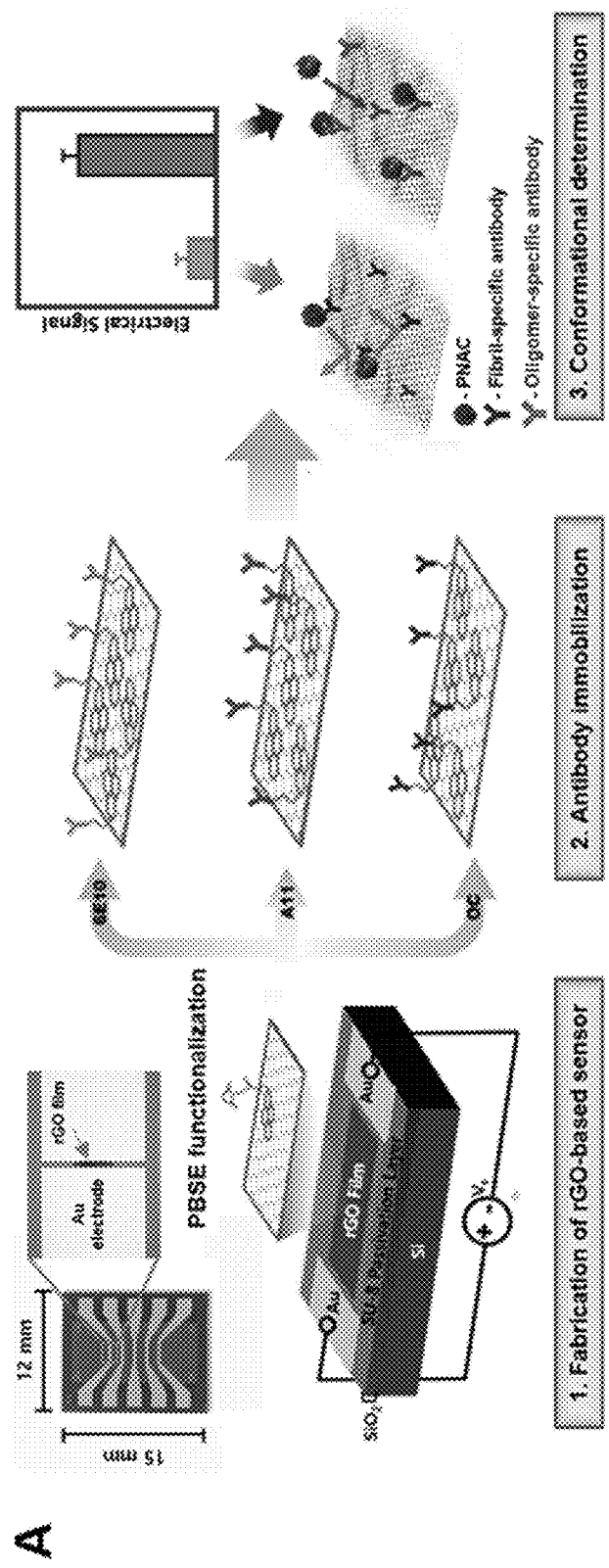
FIG. 3A schematically describes functionalization of a graphene-based sensor having three different antibodies (6E10, A11 and OC) and characterization of Aβ using the graphene-based sensor.
Figure 3B:
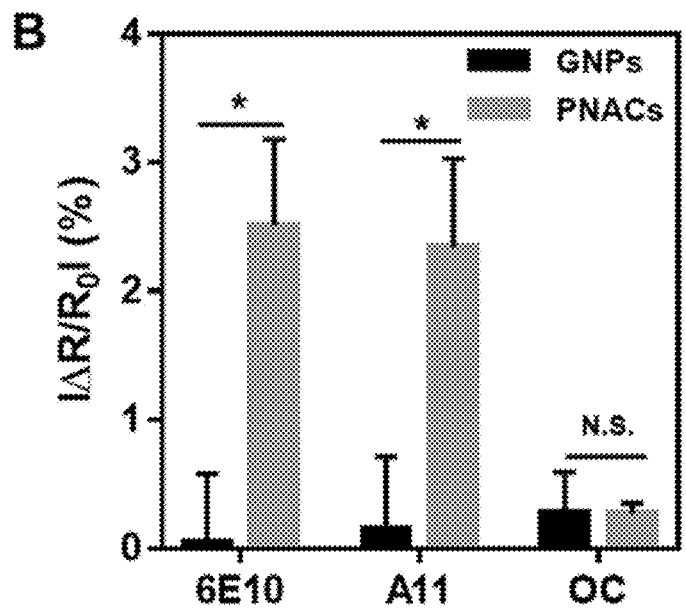
FIG. 3B shows the change in relative resistance of graphene sensors with antibodies immobilized by treatment in a comparative example and an example.
Figure 3C:
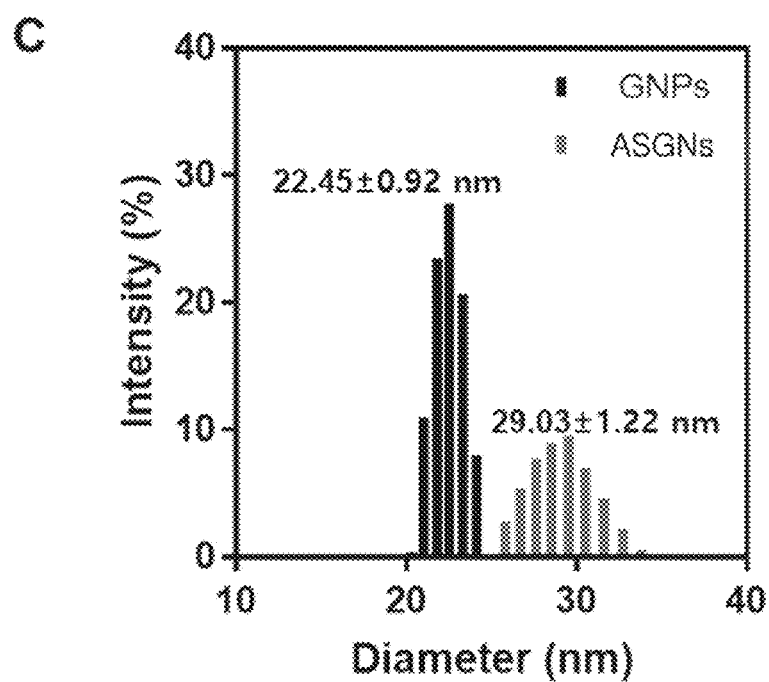
FIG. 3C shows the diameter of a gold nanoparticle of the comparative example and an amyloid shelled-gold nanoparticle of the example.
Figure 3D:
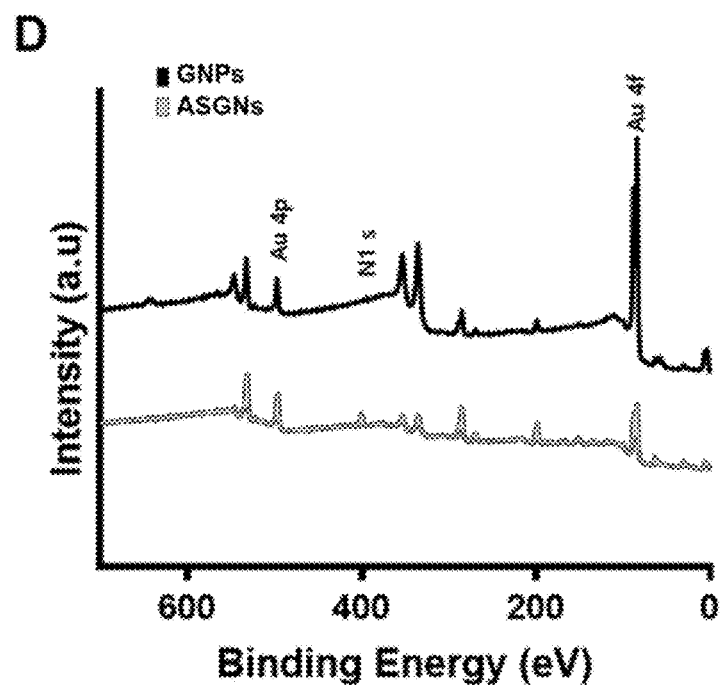
FIG. 3D shows the XPS spectra of the gold nanoparticle of the comparative example and the amyloid shelled-gold nanoparticle of the example.
Figure 3E:
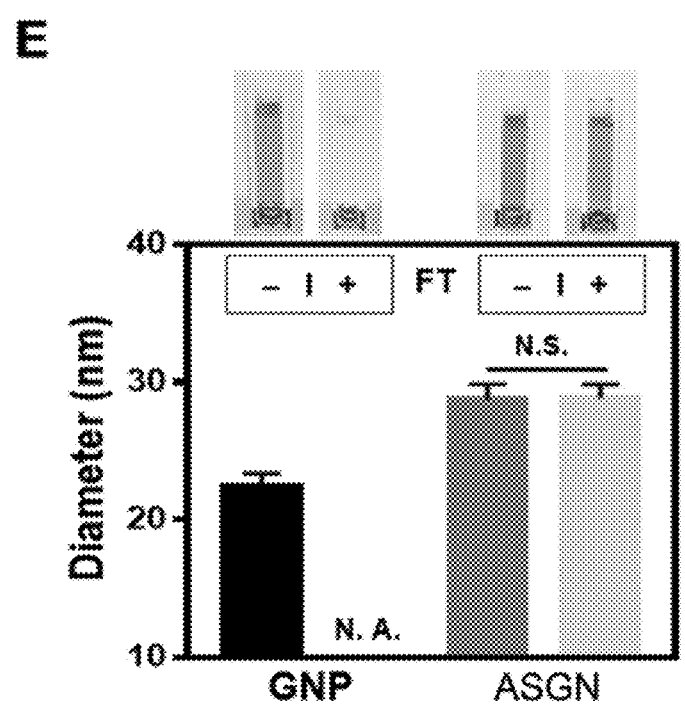
FIG. 3E shows the images of solutions of the gold nanoparticle and the amyloid shelled-gold nanoparticle and the diameter of the gold nanoparticle and the amyloid shelled-gold nanoparticle before and after freezing-thawing (FT: freezing-thawing; *p<0.0001; N.S., not significant; N.A., not applicable).

FIG. 3A schematically describes functionalization of a graphene-based sensor having three different antibodies (6E10, A11 and OC) and characterization of Aβ using the graphene-based sensor, FIG. 3B shows the change in relative resistance of graphene sensors with antibodies immobilized by treatment in a comparative example and an example, FIG. 3C shows the diameter of a gold nanoparticle of the comparative example and an amyloid shelled-gold nanoparticle of the example, FIG. 3D shows the XPS spectra of the gold nanoparticle of the comparative example and the amyloid shelled-gold nanoparticle of the example, and FIG. 3E shows the images of solutions of the gold nanoparticle and the amyloid shelled-gold nanoparticle and the diameter of the gold nanoparticle and the amyloid shelled-gold nanoparticle before and after freezing-thawing (FT: freezing-thawing; *p<0.0001; N.S., not significant; N.A., not applicable).

More specifically, after preparing graphene sensors with three different antibodies attached as shown in FIG. 3A, the reactivity with the amyloid nanoparticle was investigated. As shown in FIG. 3B, it was confirmed that 6E10 (bound to all amyloids) and A11 (bound to oligomers) showed reactivity, whereas OC (bound to amyloid fibrils) showed no reactivity. From this result, it can be seen that the protein attached on the surface of the gold-amyloid composite is an oligomer.

In addition, as a result of dynamic light scattering analysis, it was confirmed that the hydrodynamic diameter of the gold nanoparticle was increased from 22.45 nm to 29.03 nm as it was surrounded by the amyloid. This suggests that the amyloid has a thickness of about 3 nm (see FIG. 3C). The amyloid protein coating was confirmed through XPS and freeze-thaw processes (FIGS. 3D and 3E).

Test Example 2. Stability Test of Amyloid-Gold Nanoparticle Composite

The stability of the amyloid shelled-gold nanoparticle prepared in Example was tested in a PBS buffer. The result is shown in FIG. 4.

A of FIG. 4 shows the images and the shift of relative absorbance ($A_{609}/A_{525}$) of ASGN solutions of an example depending on the Aβ monomer concentration, B of FIG. 4 shows the shift of $A_{609}/A_{525}$ of a gold nanoparticle solution of a comparative example using a buffer solution, C of FIG. 4 shows the shift of $A_{609}/A_{525}$ of ASGN solutions of the example depending on the type of buffer solutions, and D of FIG. 4 the shift of relative absorbance ($A_{609}/A_{525}$) of ASGN solutions of the example in a protease XIV solution depending on time. Recording was made with 3-minute intervals.

More specifically, FIG. 4 shows a result of measuring the stability of the amyloid-gold nanoparticle in a PBS buffer while varying the ratio of the amyloid protein and the gold nanoparticle (100-2250:1). As a result of measuring relative absorbance ($A_{609}/A_{525}$), the amyloid-gold nanoparticle showed the highest stability at 1400:1.

The stability was investigated further in B and C of FIG. 4. Additionally, the color change of the amyloid-gold nanoparticle was investigated by UV-vis spectroscopy using protease XIV as a positive control. It was confirmed that the absorbance at 525 nm was decreased and the absorbance at 609 nm was increased slowly with the lapse of time.

Test Example 3. Investigation of Reactivity of Amyloid-Gold Nanoparticle Composite For investigation of the reactivity of the Amyloid Shelled-Gold Nanoparticle (ASGN), the reactivity of the amyloid-gold nanoparticle with amyloid-degrading proteases (protease XIV and matrix metallopeptidase 9 (MMP-9)) was investigated. As a result, it was confirmed that the composite of the present disclosure can be used not only for drug screening but also for investigation of the activity of an amyloid-degrading enzyme. The result is shown in FIGS. 5A to 5K.

FIGS. 5A to 5K show a result of kinetic analysis of an Aβ-degrading enzyme using ASGN of an example.

Figure 5A:
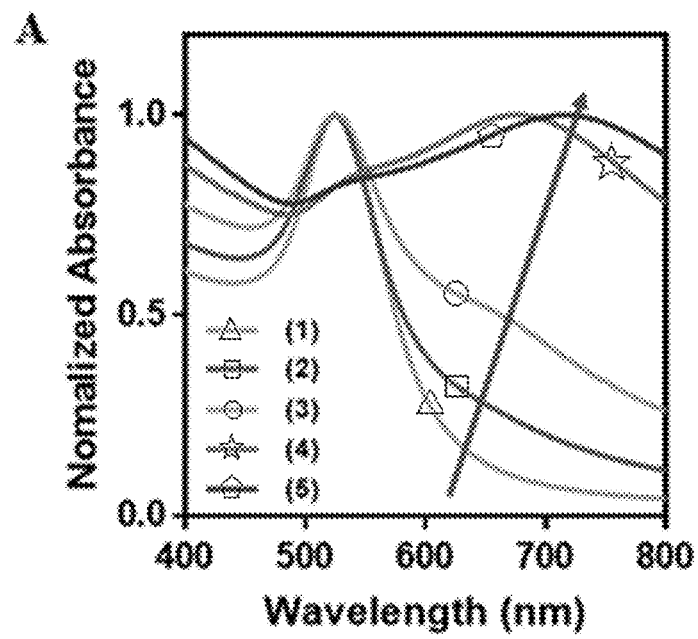
Figure 5B:
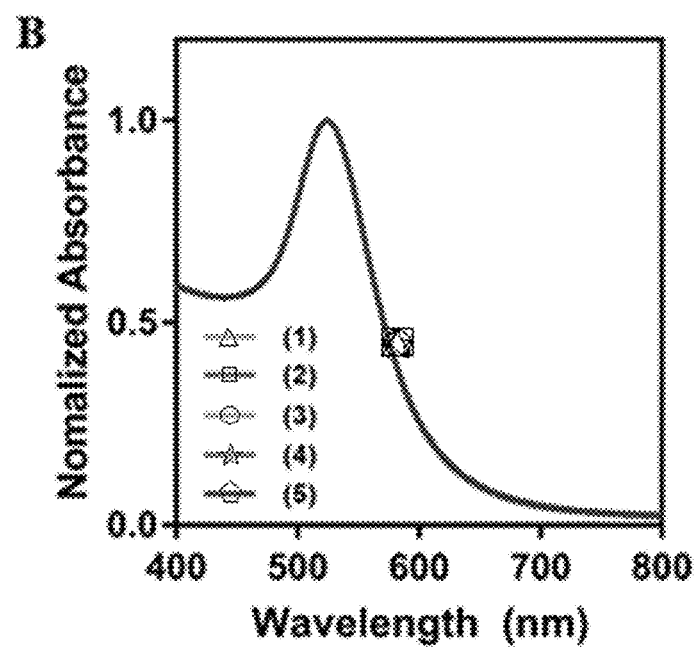
Figure 5C:
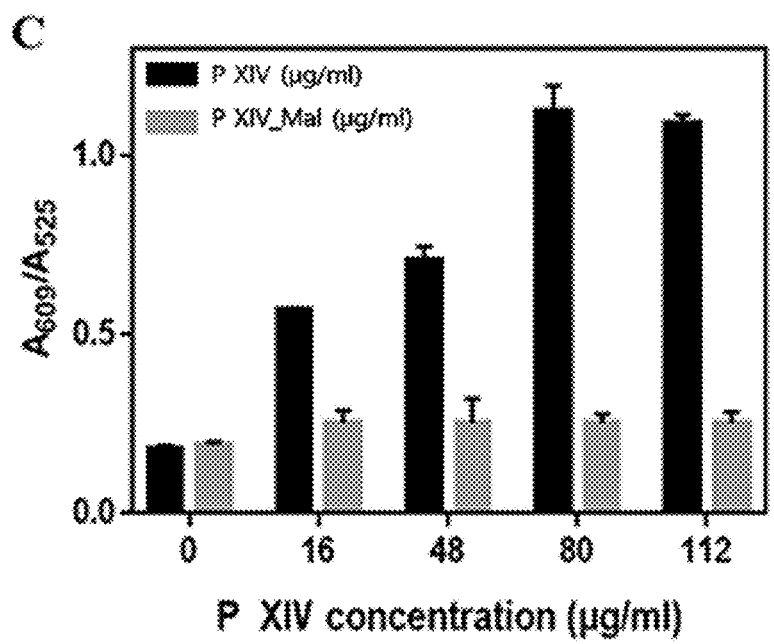
Figure 5D:
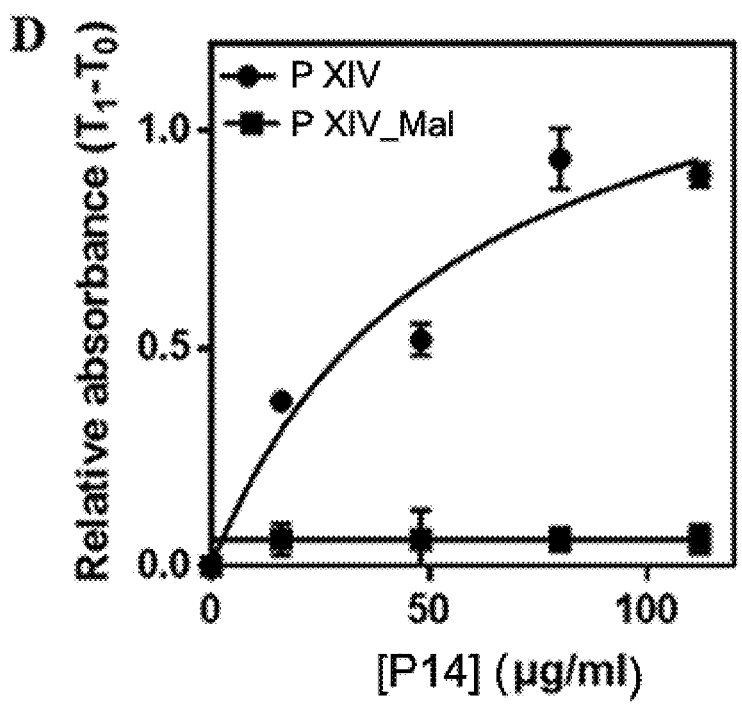

FIG. 5A shows the change in the UV-vis spectrum of activated protease XIV, and FIG. 5B shows the change in the UV-vis spectrum of deactivated protease XIV. FIGS. 5C and 5D respectively show the change in optical characteristics as a ratio of absorbance ($A_{609}/A_{525}$) and the result of Michaelis-Menten kinetics analysis. It was quantitatively confirmed that the relative absorbance is increased with the concentration of the activated protease XIV ($R^2=0.99$).

Figure 5E:
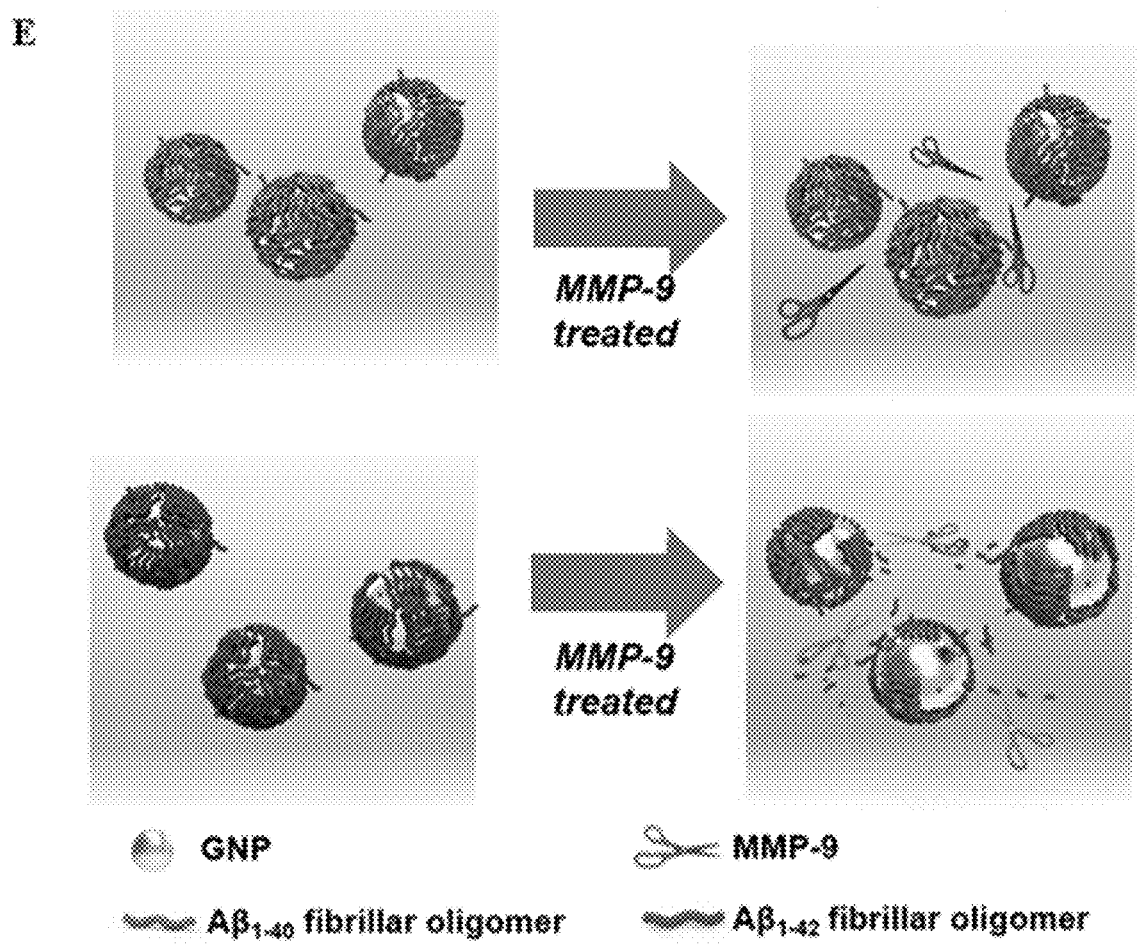
Figure 5F:
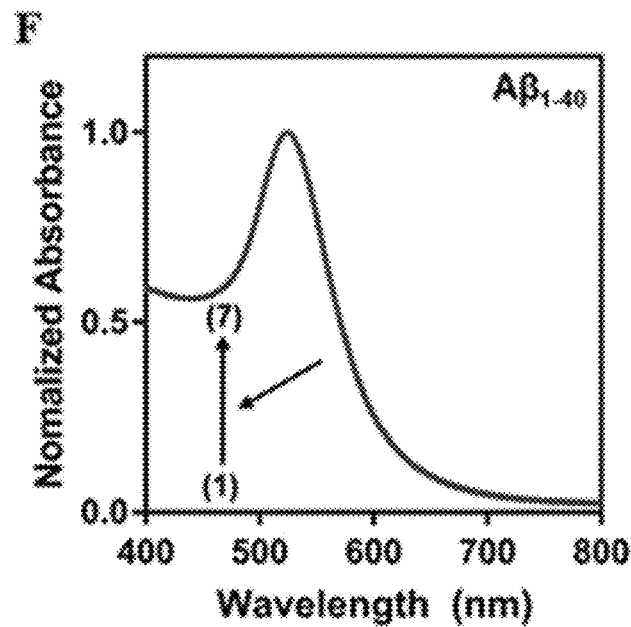
Figure 5G:
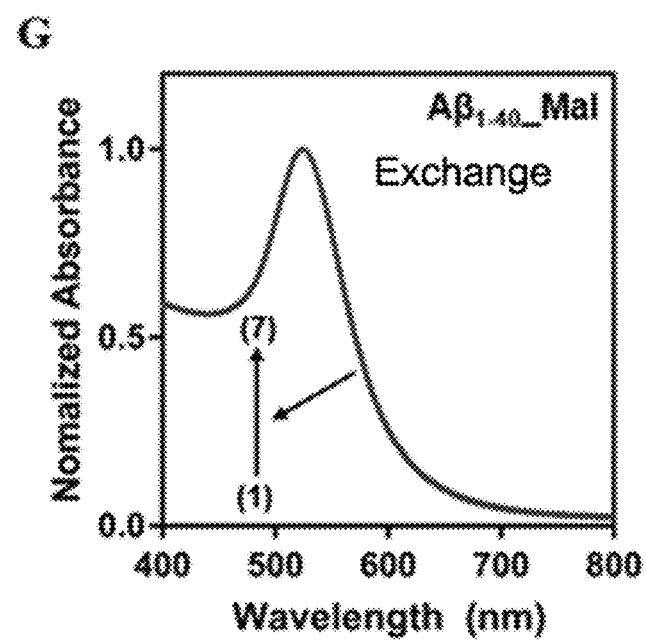
Figure 5H:
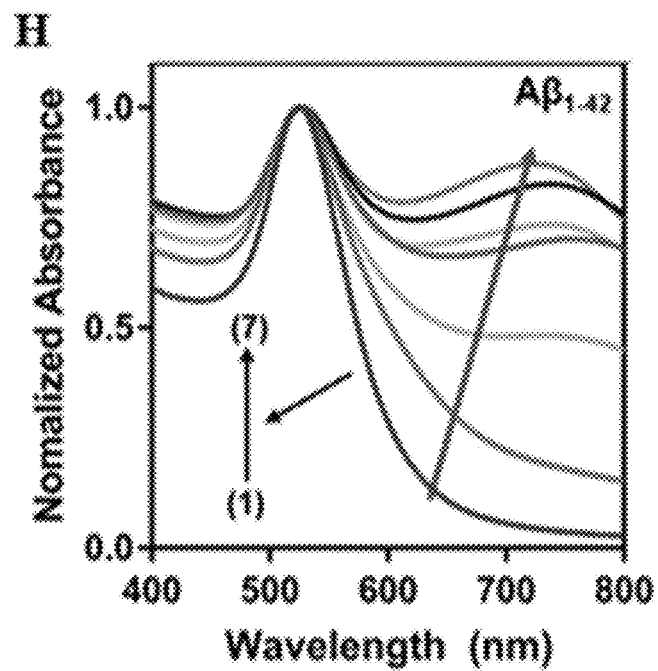
Figure 5I:
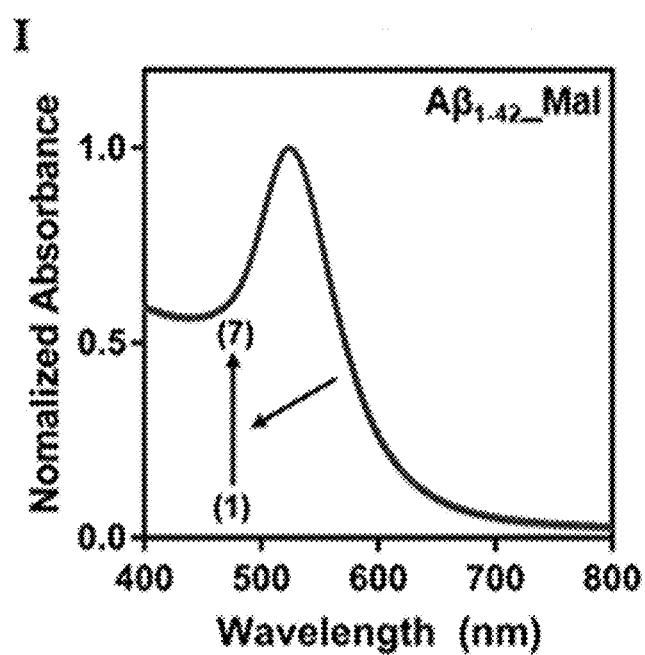
Figure 5J:
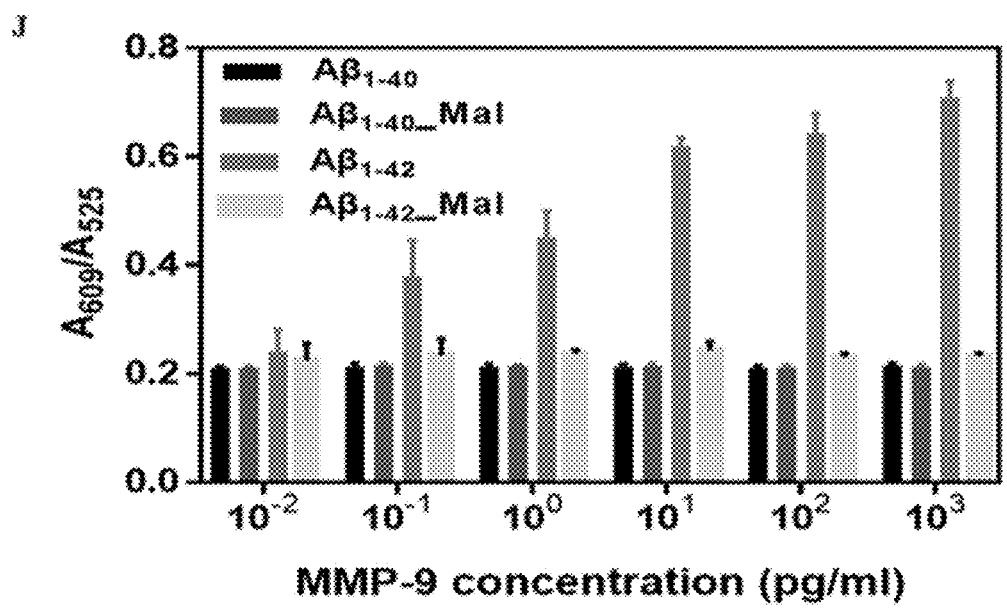
Figure 5K:
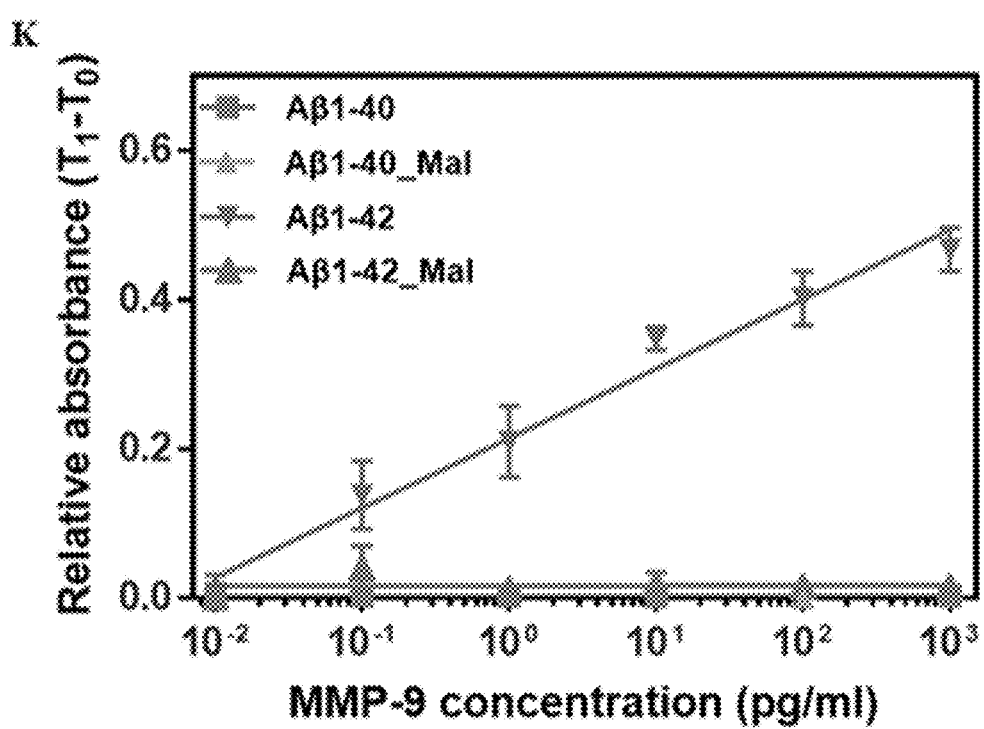

MMP-9 cannot degrade Aβ(1-40) but can degrade Aβ(1-42) (FIG. 5E). Therefore, MMP-9 degrades and removes Aβ(1-42) in the Golgi apparatus and the cytoplasm in the neurons of the brain. As shown in FIGS. 5F and 5G, the degradation activity of MMP-9 for the amyloid-gold nanoparticle was investigated for Aβ((1-40) and Aβ(1-42). Through this, it was confirmed that MMP-9 specifically degrades Aβ(1-42) only. As seen from FIGS. 5J and 5K, it was confirmed that the activity of MMP-9 can be investigated with relative absorbance.

In addition, it was investigated whether the drug-degrading effect can be detected according to the present disclosure using the drug EPPS known to degrade amyloid. The result is shown in FIG. 6.

FIG. 6 show a result of kinetic analysis of an Aβ-degrading agent (EPPS).

A of FIG. 6 shows that the change of the optical characteristics of EPPS, and B-D of FIG. 6 show the dose- and time-dependent relative absorbance curves.

Test Example 4. Drug Screening Using Amyloid-Gold Nanoparticle Composite

FIGS. 7A-7E show a result of investigating the effect of curcumin, glutathione, rutin hydrate, eptifibatide acetate and tramiprosate, which are drugs helpful for treatment of Alzheimer's disease, FIG. 7F shows dose-dependent curves for the result of FIGS. 7A-7E, and FIGS. 7G and 7H show a result of evaluating the efficacy/potency ($M^{-1}$) of the drugs.

Through these results, it was confirmed that the kit according to the present disclosure can be used for measurement of enzyme activity and drug screening.

The invention claimed is:

1. A method for screening a therapeutic agent for a neurodegenerative disease, including:
   i) a step of preparing an amyloid shelled-gold nanoparticle wherein an amyloid aggregate is formed as an amyloid protein oligomer as a coating on the surface of a gold nanoparticle;
   ii) a step of treating the amyloid shelled-gold nanoparticle with a drug candidate for a therapeutic agent for a neurodegenerative disease;
   iii) a step of comparing color change of the amyloid shelled-gold nanoparticle before and after the treatment with the drug candidate; and
   iv) a step of screening the drug candidate as a therapeutic agent for a neurodegenerative disease if the amyloid shelled-gold nanoparticle exhibits red color before treating with the drug candidate and its color changes from red to blue when treated with the drug candidate as the amyloid aggregate is degraded.

2. The method for screening a therapeutic agent for a neurodegenerative disease of claim 1, wherein the amyloid aggregate or the amyloid protein oligomer is a protein that can form an amyloid deposit selected from a group consisting of β-amyloid and tau protein of Alzheimer's disease, α-synuclein of Parkinson's disease, huntingtin of Huntington's disease, prion of prion diseases, amylin of type 2 diabetes, immunoglobulin of systemic amyloidosis, serum amyloid A and transthyretin, or a fragment thereof.

3. The method for screening a therapeutic agent for a neurodegenerative disease of claim 1, wherein the color change is measured with naked eyes, a spectrometer or a colorimeter.

4. The method for screening a therapeutic agent for a neurodegenerative disease of claim 1, wherein the amyloid shelled-gold nanoparticle exhibiting red color has a maximum absorbance at 525 nm, and has a maximum absorbance at 609 nm when its color changes from red to blue by treatment with the drug candidate as the amyloid aggregate is degraded.

* * * * *